US012577096B2

(12) United States Patent
Moult et al.

(10) Patent No.: US 12,577,096 B2
(45) Date of Patent: Mar. 17, 2026

(54) SANITISING SYSTEM FOR DRINKING WATER SYSTEMS

(71) Applicant: Zip Heaters (Aust) Pty Ltd, Condell Park (AU)

(72) Inventors: Kevin Ralph Moult, Condell Park (AU); Gary Christopher Noble, Condell Park (AU); Hayden David Scott, Condell Park (AU)

(73) Assignee: Zip Heaters (Aust) Pty Ltd, Condell Park (AU)

( * ) Notice: Subject to any disclaimer, the term of this patent is extended or adjusted under 35 U.S.C. 154(b) by 166 days.

(21) Appl. No.: 18/570,884

(22) PCT Filed: Jun. 17, 2022

(86) PCT No.: PCT/AU2022/050612
§ 371 (c)(1),
(2) Date: Dec. 15, 2023

(87) PCT Pub. No.: WO2022/261724
PCT Pub. Date: Dec. 22, 2022

(65) Prior Publication Data
US 2024/0140778 A1 May 2, 2024

(30) Foreign Application Priority Data
Jun. 17, 2021 (AU) ................................ 2021901819

(51) Int. Cl.
*B67D 1/07* (2006.01)
*A61L 2/18* (2006.01)
(Continued)

(52) U.S. Cl.
CPC .................. *B67D 1/07* (2013.01); *A61L 2/18* (2013.01); *B67D 1/1204* (2013.01);
(Continued)

(58) Field of Classification Search
CPC ...... B67D 1/07; B67D 1/1204; B67D 1/1286; B67D 1/0859; B67D 2001/0092;
(Continued)

(56) References Cited

U.S. PATENT DOCUMENTS 4,582,226 A * 4/1986 Doak ................... B67D 1/0857
137/240
5,088,517 A 2/1992 Bersch
(Continued)

FOREIGN PATENT DOCUMENTS

EP 2070866 A1 6/2009

OTHER PUBLICATIONS

Sep. 2, 2022—(WO) International Search Report and Written Opinion—App PCT/AU2022/050612.
(Continued)

*Primary Examiner* — David J Walczak
(74) *Attorney, Agent, or Firm* — Banner & Witcoff, Ltd.

(57) ABSTRACT

A system for sanitising a fluid pathway in a drinking water dispensing assembly may include: a supply of water to be delivered under pressure through the fluid pathway; and a sanitising solution to be dispensed into the fluid pathway via a flow restrictor. The flow restrictor is configured to regulate the flow rate of the solution delivered to the fluid pathway to facilitate mixing between the water and the solution to an effective sanitising concentration within the fluid pathway.

17 Claims, 4 Drawing Sheets

(51) Int. Cl.

| | |
|---|---|
| *A61L 101/20* | (2006.01) |
| *B67D 1/00* | (2006.01) |
| *B67D 1/08* | (2006.01) |
| *B67D 1/12* | (2006.01) |
| *C02F 1/68* | (2023.01) |

(52) U.S. Cl.
CPC ............ *B67D 1/1286* (2013.01); *C02F 1/686* (2013.01); *A61L 2101/20* (2020.08); *B67D 2001/0092* (2013.01); *B67D 2001/0093* (2013.01); *B67D 2001/075* (2013.01); *B67D 1/0859* (2013.01); *B67D 2210/00013* (2013.01); *C02F 2303/04* (2013.01); *C02F 2307/14* (2013.01)

(58) Field of Classification Search
CPC ...... B67D 2001/0093; B67D 2001/075; B67D 2210/00013; A61L 2/18; A61L 2101/20; C02F 1/686; C02F 2303/04; C02F 2307/14

USPC ......... 222/148; 137/101.11, 564.5; 134/22.1, 134/22.18, 166 C, 166 R, 22.11
See application file for complete search history.

(56) References Cited

U.S. PATENT DOCUMENTS

| | | | | |
|---|---|---|---|---|
| 5,090,440 A | * | 2/1992 | Ladouceur | ............... B67D 1/07 137/240 |
| 5,762,096 A | | 6/1998 | Mirabile | |
| 6,177,018 B1 | | 1/2001 | Ruppenthal | |
| 2004/0245281 A1 | | 12/2004 | Oke | |
| 2007/0204884 A1 | | 9/2007 | Moore et al. | |
| 2021/0361814 A1 | * | 11/2021 | Gordon | ..................... A61L 9/14 |

OTHER PUBLICATIONS

Apr. 7, 2025—Extended European Search Report issued in European Application No. 22823698.0.

* cited by examiner

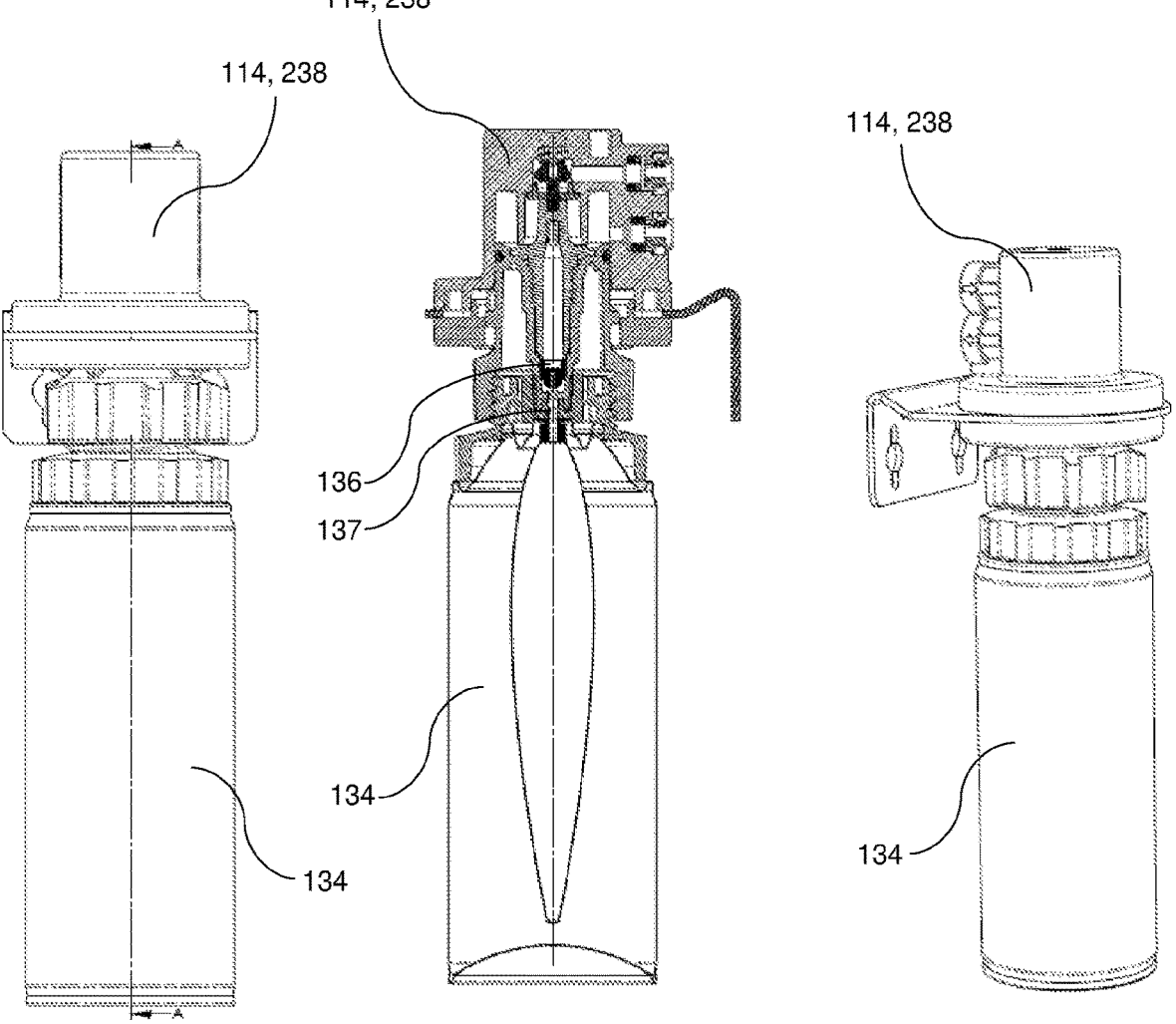
FIG. 3                    FIG. 4                    FIG. 5

300, 400

SANITISING SYSTEM FOR DRINKING WATER SYSTEMS

CROSS-REFERENCE TO RELATED APPLICATIONS

The present application claims priority from and is a U.S. National Phase of International Application No. PCT/AU2022/050612, which was filed on Jun. 17, 2022, designating the United States of America and claiming priority to the United States of America and claiming priority to Australian Patent Application No. 2021901819, filed on Jun. 17, 2021. This application claims priority to and the benefit of the above-identified applications, which are all fully incorporated by reference herein in their entireties.

FIELD

The present invention relates to a system for sanitising a fluid pathway in a drinking water dispensing assembly. The invention has primarily been developed for use with chilled drinking water dispensers, and will be described hereinafter with reference to this application.

BACKGROUND

A known chilled water dispenser typically comprises a fluid pathway that conveys filtered water to a water chilling tank, where it is then dispensed to an outlet for drinking.

A disadvantage of known chilled water dispensers is that the water contained within the fluid pathway is susceptible to common waterborne bacteria and opportunist pathogens (e.g. Legionella and Pseudomonas aeruginosa) infiltration and contamination. Water that is contaminated with Legionella bacteria or pathogens can spread into urban water systems such as residential or commercial plumbing systems and water tanks, and subsequently fed into the fluid pathway of chilled water dispensers. The water may alternatively be contaminated through back-contamination at the water outlet spouts. Filtration systems within conventional chilled water dispensers may not adequately filter out all bacteria or pathogens.

Water that is contaminated with bacteria or pathogens is particularly harmful to persons with weak immune systems or patients with respiratory illnesses, possibly occasioning death. For example, Legionella exposure can occur when a person inhales small droplets of water (e.g. from a showerhead or whilst drinking water dispensed from a chilled water dispenser) containing Legionella bacteria.

Known sanitising systems for chilled water dispensers are complex, not user-friendly and do not adequately reduce or eliminate bacteria or opportunist pathogen proliferation within the fluid pathway.

SUMMARY

It is an object of the present invention to substantially overcome, or at least ameliorate, one or more of the above drawbacks.

There is disclosed herein a system for sanitising a fluid pathway in a drinking water dispensing assembly, the system including:

a supply of water to be delivered under pressure through the fluid pathway; and a sanitising solution to be dispensed into the fluid pathway via a flow restrictor, wherein the flow restrictor is configured to regulate a flow rate of the solution delivered to the fluid pathway to facilitate mixing between the water and the solution to an effective sanitising concentration within the fluid pathway.

Preferably, the flow restrictor is a pressure-compensating flow restrictor.

Preferably, the flow rate of the sanitising solution is maintained at a rate between 0.2 litres/min to 0.3 litres/min.

Preferably, the effective sanitising concentration is between 10 to 25 ppm (mg/litres).

Preferably, the effective sanitising concentration is maintained for a dwell period within the fluid pathway.

Preferably, the dwell period is 8 minutes or more.

Preferably, the sanitising solution is stored in a consumable aerosol canister.

Preferably, a concentration of the sanitising solution stored in the canister is between 200 to 220 mg/l.

Preferably, the canister includes an inert gas pressurised to between 800 to 1000 kPa.

Preferably, the inert gas is pressurised to 900 kPa.

Preferably, the sanitising solution includes hypochlorous acid.

Preferably, the system further includes a second flow restrictor to regulate the flow rate of the supply of water through the fluid pathway to between 2.0 litres/min to 3.0 litres/min.

There is also disclosed herein a method of sanitising a fluid pathway in a drinking water dispensing assembly, the method including the steps of:

dispensing a sanitising solution into the fluid pathway via a flow restrictor;

delivering water through the fluid pathway; and regulating, by way of the flow restrictor, a flow rate of the solution dispensed into the fluid pathway to facilitate mixing between the water and the solution to an effective sanitising concentration within the fluid pathway.

Preferably, the method further includes the step of maintaining the effective sanitising concentration for a dwell period within the fluid pathway.

Preferably, the method further includes the step of emptying and cleaning the fluid pathway with water.

Preferably, the flow rate of the sanitising solution is maintained at a rate between 0.2 litres/min to 0.3 litres/min.

Preferably, the effective sanitising concentration is between 10 to 25 ppm (mg/litres).

Preferably, the effective sanitising concentration is maintained for a dwell period within the fluid pathway.

Preferably, the dwell period is 8 minutes or more.

Preferably, the sanitising solution is dispensed from a consumable aerosol container.

BRIEF DESCRIPTION OF THE DRAWINGS

Exemplary embodiments of the present disclosure will now be described, by way of examples only, with reference to the accompanying drawings and description in which:

FIG. 3 is a front view of an adaptor and canister of the system of FIG. 1 or FIG. 2;

FIG. 4 is a vertically cross-sectioned front view along line A-A of FIG. 3;

FIG. 5 is a shaded parts perspective view of the adaptor and canister of FIG. 3.

DESCRIPTION OF EMBODIMENTS

Figure 1:
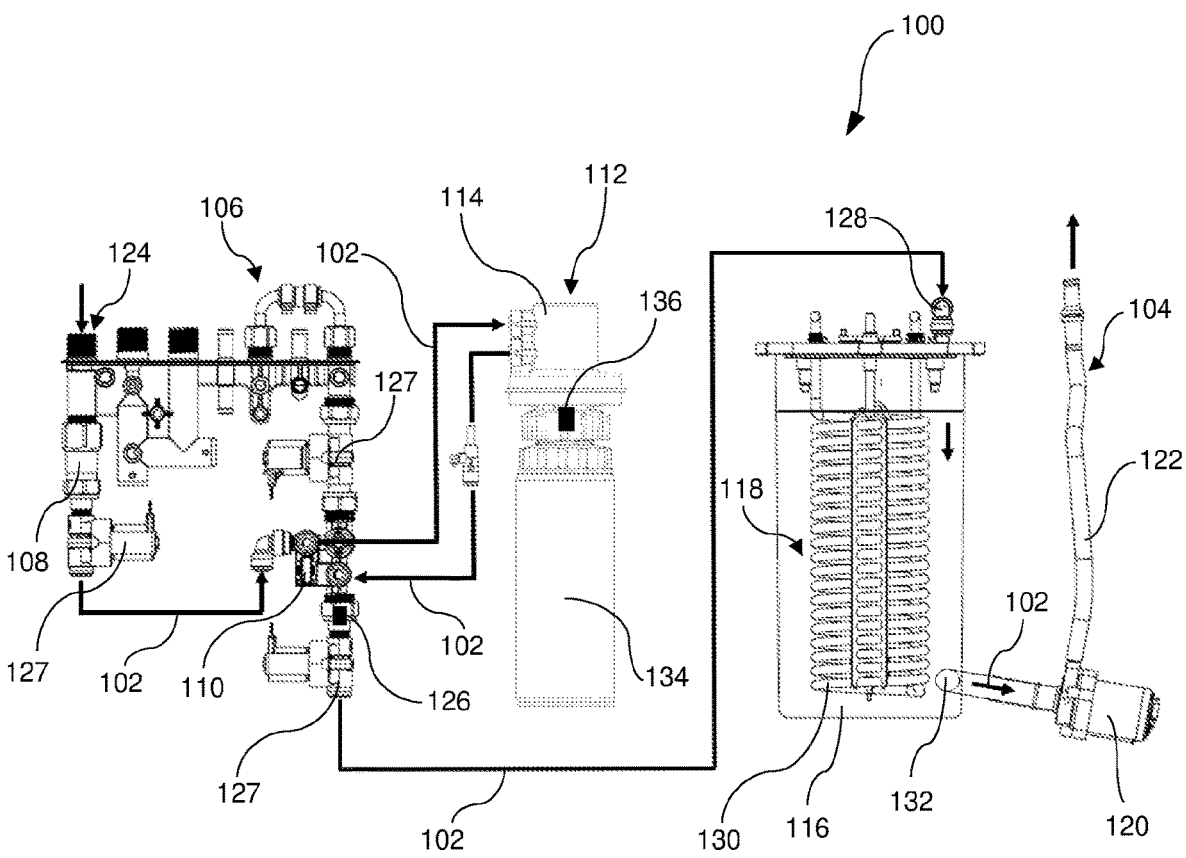
FIG. 1 is a schematic diagram of a system for sanitising a fluid pathway in a drinking water dispensing assembly according to a first embodiment.

Referring firstly to FIG. 1 of the accompanying drawings, there is schematically depicted a system 100 for sanitising a fluid pathway 102 in a drinking water dispensing assembly 104 according to a first embodiment.

In the embodiment depicted, the dispensing assembly 104 is configured as a water dispenser for dispensing chilled, ambient or heated water. The assembly 104 has a series of components fluidly connected to each other to define the fluid pathway 102. The component may include a valve assembly 106 having a pressure limiting valve (PLV) 108 and a multiport valve 110, a filter assembly 112 having a filter head manifold 114, a water storage tank 116, a refrigeration means 118, a pump 120, and a dispensing tube 122.

The valve assembly 106 includes an inlet 124 for receiving a supply of water under pressure, typically from a mains water supply. Pressure at the inlet 124 is regulated by the PLV 108 to ensure pressure within the fluid pathway 102 does not exceed 500 kPa. Water from the inlet 124 is conveyed to the filter head manifold 114 via the multiport valve, which is preferably a 5-way valve 110. Detachably removable from the filter head manifold 114 is a filter unit (not shown) to purify the water supplied from the inlet 124.

Purified water leaving the filter unit is conveyed back through the filter head manifold 114 and returned to the valve assembly 106 via the 5-way valve 110. From here, the purified water is conveyed downstream from the 5-way valve 110 to a first pressure-compensated flow regulator or restrictor 126 which is configured to maintain a constant flow rate of the purified water through the fluid pathway 102 at variable static pressures between 100-500 kPa. Flow of water through the valve assembly 106 to the tank 116 is controlled or regulated by a number of solenoid actuated valves 127. Preferably, the constant flow rate of purified water is between 2.0 litres/min to 3.0 litres/min. In many domestic or commercial purified drinking water systems, the flow rate is maintained at approximately 2.5 litres/min.

Downstream from the flow restrictor 126 is the water storage tank 116 for receiving the purified water via a tank inlet 128. The refrigeration means 118 is located within the water storage tank 116 and is in the form of a refrigeration evaporator coil 130 which is immersed in the water in the water storage tank 116 during use. The refrigeration means 118 is powered by a refrigeration power source (not shown) and is adapted to chill water in the water storage tank 116 upon activation.

A tank outlet 132 conveys the chilled purified water from the water storage tank 116 to the pump 120. The pump 120 is configured to dispense the purified water to a tap (not shown) via the dispensing tube 122.

The system 100 includes a sanitising solution to be dispensed into the fluid pathway 102. In the embodiment depicted, the sanitising solution is contained within a consumable bag-on-valve aerosol canister 134 configured to be removably attached to the filter head manifold 114 in lieu of the filter unit. During use, the canister 134 dispenses the sanitising solution under pressure to the filter head manifold 114 via a second pressure-compensated flow restrictor adaptor 136 (FIG. 4) which is configured to maintain a constant flow rate of the sanitising solution into the fluid pathway

102. Preferably, the flow rate of the sanitising solution is between 0.2 litres/min to 0.3 litres/min. In many domestic or commercial purified drinking water systems, the sanitising solution flow rate is maintained at approximately 0.25 litres/min to facilitate mixing between the water and the sanitising solution to an effective sanitising distribution within the fluid pathway 102. The effective sanitising distribution is the distribution of the sanitising solution within the water at which point waterborne bacteria or opportunist pathogen proliferation within the fluid pathway 102 is reduced or eliminated following a predetermined dwell time. Preferably, the mixed concentration of water and sanitising solution is maintained between 10 to 25 ppm, preferably 12-15 ppm (mg/L) during the predetermined dwell time. Preferably, the dwell time is 8 minutes.

In a preferred form, the aerosol canister 134 has a concentration volume of 200 mL containing Anolyte concentration of 200-220 mg/L and an inert gas (such as nitrogen) pressurised to between 800-1500 kPa, preferably 1100 kPa. In one form, the inert gas is pressurised to between 800-1000 kPa, preferably 900 kPa. Preferably, the main active ingredient of the Anolyte is hypochlorous acid to provide a sanitising solution which is non-toxic and environmentally safe.

The system 100 may also include a smart firmware protocol (not shown) to guide the user through the process of sanitising, including instruction, process flow and final dwell time, flushing and clean. The firmware may be available at automatic product commissioning stage or at a later service maintenance period.

Figure 2:
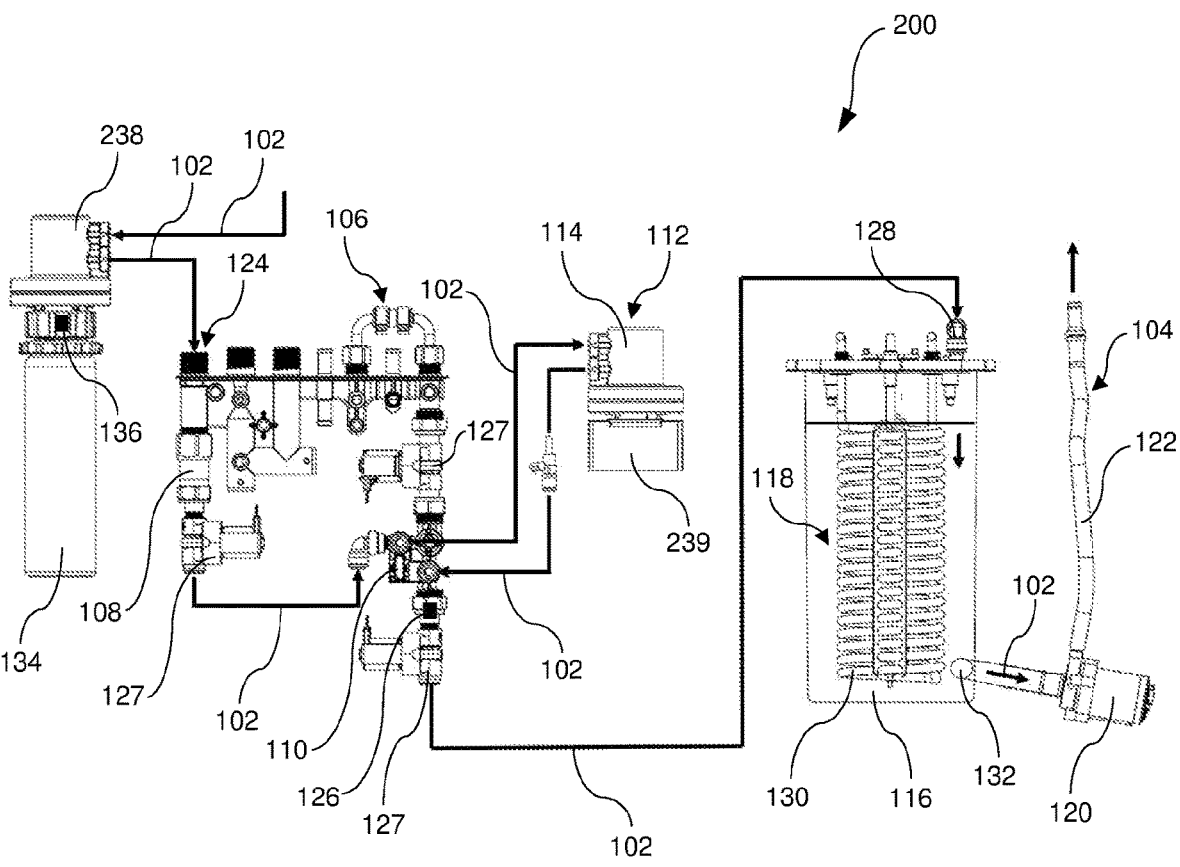
FIG. 2 is a schematic diagram of a system for sanitising a fluid pathway in a drinking water dispensing assembly according to a second embodiment.

A system 200 according to a second embodiment is depicted in FIG. 2 of the accompanying drawings. The system 200 is of an identical configuration to the system 100 of the first embodiment, apart from the point of introduction of the sanitising solution into the fluid pathway 102 which occurs upstream from the inlet 124 of the valve assembly 106 in the system 200. In this way, the system 200 is provided with a secondary filter head manifold 238 to which the aerosol canister 134 is removably attached via the adaptor 136 during use. The manifold 238 is configured to directly receive the mains water supply into which the sanitising solution is dispensed. The mixed concentration of water and sanitising solution leaves the manifold 238 where it is subsequently conveyed to the valve assembly 106 via the inlet 124. A plug 239 is inserted into the manifold 114 in lieu of the filter unit during use of the system 200.

Figure 6:
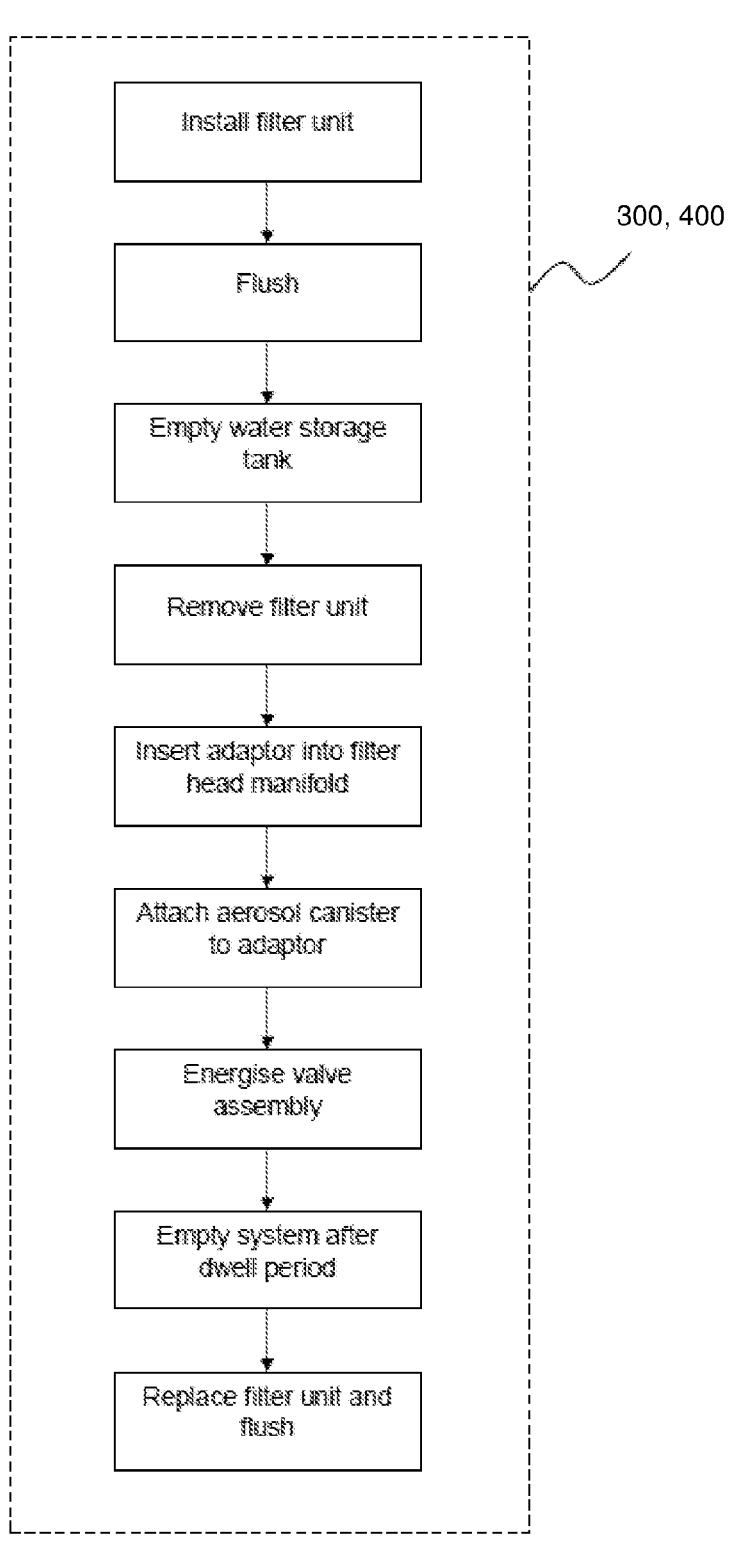
FIG. 6 is a flowchart showing steps of a process for sanitising the drinking water dispensing assembly using the system of FIG. 1 or FIG. 2.

The remaining features of the system 200 that are identical to the system 100 will thus not be further described and are provided with identical reference numerals in FIG. 2. Sanitising Process at Product Installation With reference to FIG. 6, a process 300 for sanitising the fluid pathway of the drinking water dispensing assembly 104 prior to first-use (i.e. at-installation) using the system 100 will now be described.

Initially, after the filter unit has been installed and flushed to activate the carbon and clear any carbon fines, the system 100 is configured to empty the water storage tank 116 automatically, in preparation for the sanitising process 300.

The user is then prompted to remove the filter unit, insert the adaptor 136 into the filter head manifold 114 and subsequently attach the aerosol canister 134 to the adaptor 136. Upon attachment between the canister 134 and the adaptor 136, the aerosol valve 137 (FIG. 4) is depressed and the sanitising solution enters the fluid pathway 102 until all pressures in the system 100 are equalised.

The sanitising process 300 is then commenced through acknowledgment on a user interface of the smart firmware protocol. The solenoid actuated valves 127 are energised and water flows through the fluid pathway 102, with concentration mixing occurring in the adaptor 136. The water/hypochlorous acid mixing is maintained between 10 to 25 ppm, preferably between 12 to 15 ppm, through the fluid pathway 102, making contact with all wetted surface areas for a minimum of 8 minutes (i.e. the dwell period). After this dwell period, the process 300 is configured to empty the system 100 of the water/hypochlorous acid mixture and replace the system 100 with clean potable water, fully depleting the remainder of the hypochlorous acid into the volume of the system 100 and internally rinsing the adaptor 136, aerosol valve 137 and filter head manifold 114 with clean potable water.

Final steps in the process 300 include removal of the aerosol canister 134 and adaptor 136, rinsing of the components thoroughly, and replacing the filter unit prior to a further mandatory system flush to prepare for normal use.

Sanitising Process at Regular Maintenance Periods

A process 400 for sanitising the drinking water dispensing assembly 104 at regular maintenance periods (i.e. in-field/at-home/in-office) is similar to the at-installation sanitising process, apart from the point of introduction of the sanitising solution into the fluid pathway 102 which occurs upstream from the inlet 124 of the valve assembly 106 for the process 400, that is, the process 400 utilises the system 200. This ensures the entire fluid pathway 102 has been sanitised as prior use of the dispensing assembly 104 may have higher levels of bacteria proliferation and possibly light biofilm compared to immediately after assembly of the dispensing assembly 104.

The steps of the process 300 described above are carried out for the process 400, again preferably under the guidance of the smart firmware protocol.

Should a higher level of sanitising be necessary, either a repeated process or a longer dwell time may be considered, using a variable selected dwell time setting.

Experimental testing has demonstrated the effectiveness of the systems 100, 200 at sanitising the fluid pathway 102 of the drinking water dispensing assembly 104 due to equal distribution of the sanitising solution throughout the fluid pathway 102. The ease of the sanitising processes 300, 400 using the convenient aerosol canister 134 allows for a simple and relatively clean user experience. The systems 100, 200 may also offer unskilled product owners the opportunity to sanitise their products with ease. The Anolyte may also be organically certified to offer peace of mind for users concerned about aggressive or unhealthy sanitising solutions or chemicals.

Although specific embodiments of the invention are illustrated and described herein, it will be appreciated by those of ordinary skill in the art that a variety of alternative and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", etc. are used merely as labels, and are not intended to impose numerical requirements on or to establish a certain ranking of importance of their objects.

REFERENCE NUMERAL LIST

100 System according to a first embodiment
102 Fluid pathway
104 Drinking water dispensing assembly
106 Valve assembly
108 Pressure limiting valve (PLV)
110 5-way valve
112 Filter assembly
114 Filter head manifold
116 Water storage tank
118 Refrigeration means
120 Pump
122 Dispensing tube
124 Inlet of valve assembly
126 First pressure-compensated flow restrictor
127 Solenoid actuated valve
128 Tank inlet
130 Refrigeration evaporator coil
132 Tank outlet
134 Aerosol canister
136 Second pressure-compensated flow restrictor adaptor
137 Aerosol valve
200 System according to a second embodiment
238 Secondary filter head manifold
239 Plug
300 Process using the system according to the first embodiment
400 Process using the system according to the second embodiment

The invention claimed is:

1. A system for sanitising a fluid pathway in a drinking water dispensing assembly, the system including:
a supply of water to be delivered under pressure through the fluid pathway; and
a sanitising solution to be dispensed into the fluid pathway via a flow restrictor,
wherein the flow restrictor is configured to maintain a flow rate of the sanitising solution delivered to the fluid pathway at between 0.2 litres/min to 0.3 litres/min, and wherein the flow restrictor is configured to mix the water and the sanitising solution to an effective sanitising concentration of between 10 to 25 ppm (mg/litres) within the fluid pathway, and
wherein the system is configured to maintain the effective sanitising concentration for a predetermined dwell period within the fluid pathway.

2. The system of claim 1, wherein the flow restrictor is a pressure-compensating flow restrictor.

3. The system of claim 1, wherein the flow restrictor is adapted to maintain the flow rate of the sanitising solution at 0.25 litres/min.

4. The system of claim 1, wherein the effective sanitising concentration is between 12 to 15 ppm (mg/litres).

5. The system of claim 1, wherein the predetermined dwell period is 8 minutes or more.

6. The system of claim 1, wherein the sanitising solution is stored in a consumable aerosol canister.

7. The system of claim 6, wherein a concentration of the sanitising solution stored in the canister is between 200 to 220 mg/l.

8. The system of claim 6 or claim 7, wherein the canister includes an inert gas pressurised to between 800 to 1000 kPa.

9. The system of claim 8, wherein the inert gas is pressurised to 900 kPa.

10. The system of claim 1, wherein the sanitising solution includes hypochlorous acid.

11. The system of claim 1, further including a second flow restrictor to regulate the flow rate of the supply of water through the fluid pathway to between 2.0 litres/min to 3.0 litres/min.

12. A method of sanitising a fluid pathway in a drinking water dispensing assembly, the method including the steps of:

dispensing a sanitising solution into the fluid pathway via a flow restrictor;

delivering water through the fluid pathway;

maintaining, by way of the flow restrictor, a flow rate of the sanitising solution dispensed into the fluid pathway at between 0.2 litres/min to 0.3 litres/min to facilitate mixing between the water and the sanitising solution to an effective sanitising concentration of between 10 to 25 ppm (mg/litres) within the fluid pathway; and maintaining the effective sanitising concentration for a predetermined dwell period within the fluid pathway.

13. The method of claim 12, further including a step of emptying and cleaning the fluid pathway with water.

14. The method of claim 12, wherein the flow rate of the sanitising solution is maintained at a rate of 0.25 litres/min.

15. The method of claim 12, wherein the effective sanitising concentration is between 12 to 15 ppm (mg/litres).

16. The method of claim 12, wherein the predetermined dwell period is 8 minutes or more.

17. The method of claim 12, wherein the sanitising solution is dispensed from a consumable aerosol container.

* * * * *